US011386283B2

(12) United States Patent
Mueller-Wehlau

(10) Patent No.: US 11,386,283 B2
(45) Date of Patent: Jul. 12, 2022

(54) METHOD FOR OPERATING AN APPARATUS FOR TINNITUS CHARACTERIZATION AND CORRESPONDING APPARATUS

(71) Applicant: SIVANTOS PTE. LTD., Singapore (SG)

(72) Inventor: Matthias Mueller-Wehlau, Nuremberg (DE)

(73) Assignee: Sivantos Pte. Ltd., Singapore (SG)

( * ) Notice: Subject to any disclaimer, the term of this patent is extended or adjusted under 35 U.S.C. 154(b) by 278 days.

(21) Appl. No.: 16/202,189

(22) Filed: Nov. 28, 2018

(65) Prior Publication Data
US 2019/0163952 A1 May 30, 2019

(30) Foreign Application Priority Data

Nov. 30, 2017 (DE) ...................... 10 2017 221 611.5

(51) Int. Cl.
*G06K 9/00* (2022.01)
*A61B 5/12* (2006.01)
(Continued)

(52) U.S. Cl.
CPC ............ *G06K 9/0053* (2013.01); *A61B 5/128* (2013.01); *G06K 9/00543* (2013.01);
(Continued)

(58) Field of Classification Search
CPC ......... A61B 5/128; A61B 5/121; A61B 5/123; H04R 25/75; H04R 25/505; G06K 9/0053
See application file for complete search history.

(56) References Cited

U.S. PATENT DOCUMENTS

| | | |
|---|---|---|
| 9,549,269 B2 | 1/2017 | Nötzel et al. |
| 9,712,933 B2 | 7/2017 | Pontoppidan |
| | (Continued) | |

FOREIGN PATENT DOCUMENTS

| | | |
|---|---|---|
| CN | 102821346 A | 12/2012 |
| DE | 10128642 A1 | 1/2002 |
| | (Continued) | |

OTHER PUBLICATIONS

David M Baguley, Mechanisms of tinnitus, Oct. 2002, British Medical Bulletin, vol. 63, Issue 1, pp. 195-212 (Year: 2002).*
(Continued)

*Primary Examiner* — Daniel L Cerioni
*Assistant Examiner* — Jonathan E. Cooper
(74) *Attorney, Agent, or Firm* — Laurence A. Greenberg; Werner H. Stemer; Ralph E. Locher

(57) ABSTRACT

A method operates an apparatus for tinnitus characterization, in which, in a first step, a broadband test signal having a number of signal frequencies is generated and compared with a tinnitus noise. The respective test signal is stored with an associated comparison result. A probability correlation for determining the tinnitus noise is established based on the stored test signals and comparison results. In a second step, the amplitudes of the individual signal frequencies of the test signal are varied. The first and second steps are performed repeatedly until the probability correlation reaches or exceeds a first threshold value. In a third step, the amplitudes of the individual signal frequencies of the test signal are varied with reference to the probability correlation.

5 Claims, 2 Drawing Sheets

(51) Int. Cl.
*H04R 25/00* (2006.01)
*G10K 11/175* (2006.01)

(52) U.S. Cl.
CPC ......... *G10K 11/1752* (2020.05); *H04R 25/75* (2013.01); *H04R 25/505* (2013.01)

(56) References Cited

U.S. PATENT DOCUMENTS

| | | | |
|---|---|---|---|
| 2010/0232631 A1* | 9/2010 | Klefenz | A61N 1/36038 381/313 |
| 2015/0073296 A1* | 3/2015 | Zeng | A61B 5/128 600/559 |
| 2017/0042739 A1* | 2/2017 | O'Neill | A61F 11/00 |

FOREIGN PATENT DOCUMENTS

| | | | | |
|---|---|---|---|---|
| DE | 102007046020 A1 | 4/2009 | | |
| DE | 102012220620 A1 | 5/2014 | | |
| WO | WO-2007121446 A2 * | 10/2007 | ............. | H04R 25/75 |

OTHER PUBLICATIONS

Jos J. Eggermont, On the pathophysiology of tinnitus; A review and a peripheral model, 1990, Hearing Research, vol. 48, Issues 1-2, pp. 111-123, (Year: 1990).*

Marmel, F., Plack, C. J., Hopkins, K., Carlyon, R. P., Gockel, H. E., & Moore, B. C, The role of excitation-pattern cues in the detection of frequency shifts in bandpass-filtered complex tones, 2015, The Journal of the Acoustical Society of America, 137(5), 2687-2697 (Year: 2015).*

\* cited by examiner

METHOD FOR OPERATING AN APPARATUS FOR TINNITUS CHARACTERIZATION AND CORRESPONDING APPARATUS

CROSS-REFERENCE TO RELATED APPLICATION

This application claims the priority, under 35 U.S.C. § 119, of German application DE 10 2017 221 611.5, filed Nov. 30, 2017; the prior application is herewith incorporated by reference in its entirety.

BACKGROUND OF THE INVENTION

Field of the Invention

The invention relates to a method for operating an apparatus for tinnitus characterization and to a corresponding apparatus.

The hearing impairment brought about by hearing loss often triggers neuroplastic reorganization of the central auditory system in the affected person's brain, and accordingly is often a trigger and cause of the occurrence of (chronic) tinnitus.

Tinnitus, or ringing in the ears, refers generally to all types of head or ear noises that are not caused by acoustic signals from the environment that are conducted into the ear. Although tinnitus is innocuous, it puts great strain on many affected persons. For example, the affected person's concentration is disturbed and sleep problems arise. In particular, chronic tinnitus often leads to serious psychological problems and thus sometimes has a negative effect on the professional and social life of the person affected.

In the course of tinnitus therapy, noise devices (tinnitus noisers, audio stimulators, tinnitus control instruments, tinnitus maskers) are often used. In this way, a tinnitus therapy apparatus similar to a hearing aid, known as a noiser or masker, offers the affected person an acoustic signal in the form of a quiet, relatively unobtrusive sound, which is intended to cover ("mask") the tinnitus or to serve as a distraction.

By way of example, Notch therapies are also possible in which an acoustic signal from the environment is generated for the affected person, in which one or more of the tinnitus frequencies of the perceived tinnitus noise are suppressed. This makes possible a neuroplastic reorganization of the affected person's central auditory system, which reverses the tinnitus-causing maladaptive neuroplastic reorganization of the affected person's central auditory system.

For effective therapy or treatment, however, it is always necessary to identify and characterize as exactly as possible the tinnitus noise that the affected person perceives, and specifically the or each tinnitus frequency and its respective amplitude or intensity.

To characterize tinnitus noise, tinnitus analysis (or tinnitus matching) is usually performed. For this purpose, for example, tinnitus characterization apparatus may be conceived that have a signal generator for generating audio signals or acoustic test tones, which are played back to the affected person for example by means of a headphone.

In tinnitus analysis or tinnitus matching, the affected person is usually presented with two (test) tones whose respective tone or signal frequencies have a predefined frequency difference from one another. The affected person compares the (external) tones with the person's perceived (internal) tinnitus noise, and two new tones with two new tone frequencies are then generated based on the comparison. The frequency step size of the new tones is successively reduced with each comparison, so that with each comparison, the tones are successively closer to the perceived tinnitus noise, or the or each tinnitus frequency.

However, this kind of tinnitus matching by means of comparison measurements has some drawbacks. Unpracticed listeners in particular often find it difficult to reliably compare the test tones they are presented with to the tinnitus noise they perceive. This impairs reproducibility and accuracy, so that the matching results have a comparatively high variability. In particular, the problem known as octave confusion often occurs. In octave confusion, the tones of the tinnitus frequency that the affected person identifies deviate from the correct tinnitus frequency by one octave higher or lower. This occurs in particular in the case of tinnitus noises that do not consist only of a single (pure) tone or tinnitus frequency, but have a number of different tinnitus frequencies.

Depending on the number of comparisons of the generated test tones with the tinnitus noise, the frequency step size, and thus the frequency resolution, is limited by the extent to which the affected person is able to reliably identify the person's own tinnitus noise and correctly assign it to the respective tones. For example, Notch therapies require a comparatively high frequency resolution of the or each tinnitus frequency, so that such tinnitus matching becomes particularly time consuming.

In addition to identifying the or each tinnitus frequency, it is typically necessary to identify the amplitude of the or each tinnitus frequency in the perceived tinnitus noise. Often, at the beginning of the tinnitus matching, the volume of the generated (test) tones is adjusted until it corresponds approximately to the volume of the perceived tinnitus noise. But because this volume adjustment typically occurs at a (tone) frequency that differs from the or each tinnitus frequency, it is not assured that the amplitude identified will correspond to the actual amplitude at the or each tinnitus frequency. Particularly in affected persons who have additional hearing loss, there are often substantial deviations between the identified amplitudes and actual amplitudes of the tinnitus noise.

SUMMARY OF THE INVENTION

The objective of this invention is to provide a particularly suitable method for operating an apparatus for tinnitus characterization. In particular, the invention is intended to make it easier for an affected person to reliably identify the tinnitus noise. An additional objective of the invention is to provide a suitable apparatus for such a method.

The objective is achieved according to the invention, with regard to the method, by means of the features of the independent method claim, and with regard to the apparatus, by means of the features of the independent apparatus claim. Advantageous configurations and developments of the invention are the subject matter of the respective dependent claims.

The method according to the invention is suitable and configured for operating an apparatus for tinnitus characterization.

According to the method, in a first step, a broadband test signal having a number of signal frequencies is generated as an acoustic signal or audio signal and compared with a tinnitus noise. For each test signal presented, a comparison is made with the tinnitus noise and it is assessed whether the test signal masks the perceived tinnitus or not. The respective test signal is stored together with the associated comparison result. In particular, positive comparison results in which the tinnitus noise is masked by the test signal, and negative comparison results in which the test signal does not or only partially mask the tinnitus, are both evaluated.

Based on the stored comparison results and test signals, a probability correlation (likelihood correlation) is established for determining the tinnitus noise. This means that the probability correlation is established based on the test signals, reflecting the masking effect. In other words, in the first step, an occlusion measurement of the tinnitus noise is carried out, and the probability correlation is derived from the occlusion or masking properties of the test signals.

In a second step, the amplitudes of the individual signal frequencies of the test signal are varied. The first and second steps are performed repeatedly until the probability correlation reaches or exceeds a first threshold value. In other words, the test signal is altered and then compared with the tinnitus noise again. This process is successively repeated, generating additional comparison results, until the probability correlation reaches or exceeds the first threshold value. The first threshold value substantially corresponds to a minimum number of, in particular, positive comparison results or stored test signals, which are needed in order to establish a suitable probability correlation.

In a third step, if the first threshold value is reached or exceeded, the amplitudes of the individual signal frequencies of the test signal are varied with respect to the probability correlation. That is to say, a test signal is estimated, with reference to the comparison results or masking effects, that plausibly reproduces the tinnitus noise; the plausibility is increasingly improved as the number of comparison results increases. Establishing the most plausible probability correlation possible thus substantially corresponds to the characterization of the tinnitus noise. In this way, a particularly suitable method for operating an apparatus for tinnitus characterization is realized.

Thus, the comparatively difficult task of identifying individual tinnitus frequencies is simplified in that a broadband test signal is generated and the affected person compares this test signal with regard to masking, obscuring or occluding the person's perceived tinnitus noise. In other words, the affected person assesses whether they perceive their tinnitus noise while the test signal is being played or presented.

In contrast to the prior art, the affected person thus does not compare individual (sound) frequencies with one another, but merely evaluates whether or not the test signal accomplishes a masking. This means that instead of a comparison measurement, an occlusion measurement is carried out, as a result of which, in particular, the risk of octave confusion is substantially entirely avoided. As a result, a particularly suitable tinnitus characterization is also realized for unpracticed listeners.

As a result of successively generating new (modified) test signals, the tinnitus noise, i.e. the or each tinnitus frequency as well as the respective amplitude, may be reliably identified by means of the probability correlation established based on the test signals.

The broadband test signals in this case each respectively contains a number of signal frequencies. This means that the test signals are composed of a number of (spectrally) juxtaposed, narrowband or tonal noise components.

The test signal is suitably played or presented to the affected person for a sufficiently long time that the person may reliably compare the test signal to the tinnitus noise. In other words, the affected person checks whether they are able to perceive their tinnitus noise in the presence of the test signal. After the affected person responds, the amplitudes of the test signal's individual signal frequencies or narrowband noises are varied. The probability correlation is determined from the comparison results, and is used in the third step in order to set or vary the narrowband noises selectively. This ensures a fast and reliable identification of the tinnitus noise.

In an advantageous embodiment, the first and third steps are repeated several times until the probability correlation reaches or exceeds a second threshold value. The second threshold value is suitably a minimum probability or a probability measure that the test signal derived from the probability correlation corresponds to the actual tinnitus noise. If the probability correlation reaches or exceeds the second threshold value, the method terminates and the test signal that may be identified based on the probability correlation is stored in memory and/or output as an acoustic signal that corresponds to the tinnitus noise. In this way, a particularly effective tinnitus characterization is realized.

In a suitable development, in the second step, the amplitudes of the individual signal frequencies or narrowband noises of the test signal are set at random. Suitably, at the start of the method, i.e. in the first comparison, a test signal is used that has random amplitude values for the individual signal frequencies. This accounts for the fact that the tinnitus noise is substantially unknown when the method begins. The random amplitude distribution of the signal frequencies makes it possible to identify the probability correlation and thus the tinnitus noise particularly effectively.

In an expedient embodiment of the method, a physiological model of an ear, or of a section or part of the ear, is used to establish the probability correlation. A "physiological model" here refers in particular to a mathematical and/or computer or programmatic model for describing or simulating a physiological component of the ear or a physiological function of such a component. Put differently, the physiological model makes it possible to establish the ear's physiological properties or reactions. In this way, a particularly suitable method is realized. In particular, for input variables, the signal frequencies and amplitudes of those test signals that have a positive comparison result are used.

In a preferred embodiment, a model of a basilar membrane is used as the physiological model, and the probability correlation is established with reference to an excitation pattern of the modeled basilar membrane.

The pitch that an affected person perceives, in the case of a sound having an acoustic signal of a certain frequency, is closely related to the location on the basilar membrane where an excitation maximum exists at this frequency. The arousal pattern caused by an acoustic signal of a specific first frequency is not sharply localized in one region of the basilar membrane, but also leads to excitation or arousal in regions of the basilar membrane spatially adjacent to that region. This spatially extended excitation yields the effect of an auditory masking or spectral occlusion, in which a tone of a second frequency may not be perceived when the excitation on the basilar membrane caused by this tone is less than that of an adjacent tone of higher intensity.

By establishing an excitation or arousal pattern of a modeled basilar membrane, it is thus possible to establish a particularly suitable and reliable probability correlation. In particular, in this way it is possible to take into account physiological factors in identifying the tinnitus noise, particularly auditory masking in which the presence of a first tone makes a second quieter tone imperceptible.

In consequence, an excitation pattern is calculated for each comparison result and is correlated with the excitation patterns of previous comparison results. The similarities of the excitation patterns that may be established in this way allow a particularly reliable determination of the or each tinnitus frequency and the respective (tinnitus) amplitude.

In modeling the basilar membrane and/or identifying the excitation or arousal pattern, it is possible to take into account any hearing loss or hearing damage that the affected person may have. In other words, it is possible to use hearing thresholds of the affected person in modeling the basilar membrane, which further improves the accuracy of the probability correlation, and thus the identification of the tinnitus noise.

In a preferred application, the above-described method is used to operate an apparatus for tinnitus characterization. The apparatus contains, for example, a signal generator for generating an acoustic test signal, as well as a receiver, for example a headphone, by which the test signal may be presented or output to an affected person. The apparatus in this case preferably has a controller (i.e. a control unit).

This controller is generally set up—by programming and/or circuitry—to carry out the above-described method according to the invention. The controller is thus in particular devised so as to vary the test signal based on the responses of the affected person, i.e. based on the comparison results, and to establish a probability correlation, in particular by identifying an excitation pattern based on a physiological model of a basilar membrane.

The controller is respectively formed, at least in essence, by a microcontroller with a processor and a data memory in which the functionality for carrying out the method according to the invention is implemented by programming, in the form of operating software (firmware), so that the method is carried out automatically—and optionally in interaction with a user—when executing the operating software in the microcontroller.

Alternatively, in one possible embodiment that is within the scope of the invention, the controller is also formed by programmable electronic components, for example an application-specific integrated circuit (ASIC), in which the functionality for carrying out the method according to the invention is implemented by means of circuitry.

As a result, a particularly suitable apparatus is realized. The method according to the invention makes it easier for an unpracticed listener to determine the perceived tinnitus noise reliably and with high accuracy when using the apparatus. By evaluating the probability based on a physiological excitation pattern of the modeled basilar membrane, it is also possible to use broadband test signals and on that basis to reliably determine both the individual tinnitus frequencies and the amplitudes of the respective tinnitus noise.

Other features which are considered as characteristic for the invention are set forth in the appended claims.

Although the invention is illustrated and described herein as embodied in a method for operating an apparatus for tinnitus characterization and corresponding apparatus, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Figure 1:
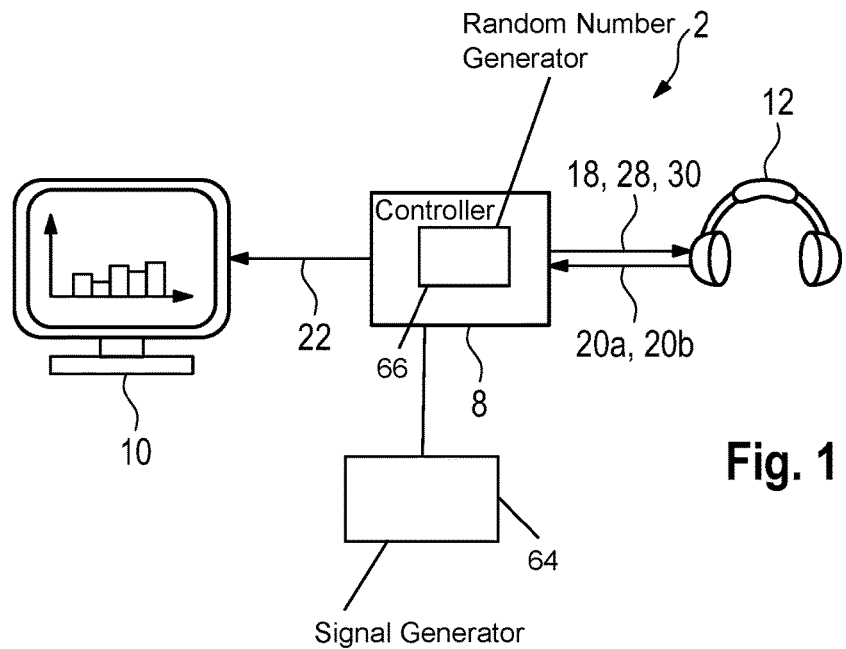
FIG. 1 is a simplified illustration of an apparatus for tinnitus characterization according to the invention.

Corresponding parts and sizes are always assigned the same reference numerals in all drawings.

Figure 2:
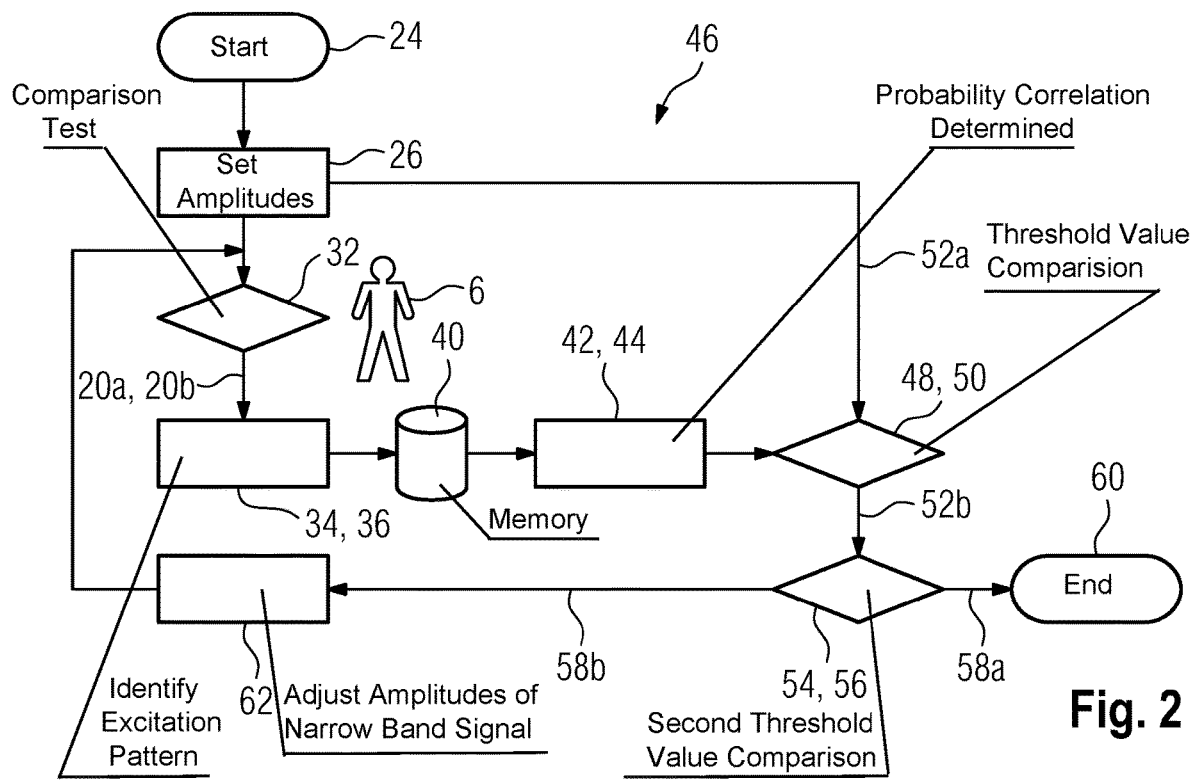
FIG. 2 is flow diagram of a method for operating the apparatus.

Referring now to the figures of the drawings in detail and first, particularly to FIG. 1 thereof, there is shown a simplified and schematic illustration of, an apparatus 2 for tinnitus characterization, i.e. for determining a tinnitus noise 4 (FIG. 3, FIG. 4) of an affected person 6 (FIG. 2). The apparatus 2, in substance, has a controller 8 as a control device, a display unit 10 and a headphone 12.

In the course of tinnitus characterization, the tinnitus noise 4 (FIG. 3, FIG. 4) of the affected person 6 is determined as accurately as possible with regard to one or each perceived tinnitus frequency 14 and its respectively assigned (tinnitus) amplitude 16. For this purpose, the affected person 6 puts on the headphone 12, so that the person perceives no ambient acoustic signals, as far as possible, during the characterization. By means of a signal generator 64 controlled by the controller 8, a broadband test signal 18 is generated and played back to the affected person 6 as an acoustic signal or audio signal by means of the headphone 12.

The affected person 6 compares the presented test signal 18 with the person's perceived tinnitus noise 4, and the test signal 18 is varied based on a respective comparison result 20a, 20b. The spectrum of the test signal 18 and the comparison results 20a, 20b are transmitted to the display unit 10, for example as image data 22, and presented to a user, in particular an ENT specialist or hearing aid acoustician. By way of example, it is also conceivable that the affected person 6 may operate the apparatus 2 and carry out the method on their own.

In FIG. 2, a method for operating the apparatus 2 is illustrated by means of a flow diagram, and this method is explained in greater detail below.

After a start 24 of the method, in step 26 the broadband test signal 18 is generated. The test signal 18 has—as shown in particular in FIGS. 3 and 4—a number of signal frequencies or narrowband signals 28 that are aligned with regard to frequency. In the exemplary embodiment of FIGS. 3 and 4, the test signal 18 has, for example, seven narrowband signals 28. The narrowband signals 28 or the test signal 18 are then suitably generated within a frequency range of the tinnitus noise 4.

Each narrowband signal 28 has a respective (signal) amplitude 30, and the amplitudes 30 of the narrowband signals 22 are set at random in step 26. In other words, the controller 8 has for example a random number generator 66 by means of which the amplitudes 30 are varied in step 26.

In a subsequent comparison 32, the test signal 18 is presented to the affected person 6 by means of the headphone 12. The affected person 6 compares the test signal 12 with the tinnitus noise 4, and in particular the affected person 6 checks whether the test signal 18 masks, i.e. covers or occludes, the tinnitus noise 4. In other words, the affected person 6 evaluates whether the tinnitus noise 4 is still perceived on playback of the test signal 18. The test signal 18 is played or presented to the affected person 6 for a sufficiently long time that the person may reliably compare the test signal 18 to the tinnitus noise 4. Thus, in substance, the comparison 32 measures the occlusion of the tinnitus noise 4 by the test signal 18.

After a negative comparison result 20a in which the tinnitus noise 4 is not masked by the test signal 18, or after a positive comparison result 20b in which the tinnitus noise 4 is masked by the test signal 18, in step 26, the amplitudes 30 of the narrowband signals 28 of the test signal 18 again are varied randomly or based on the previous results, and a step 34 is started.

A physiological model 36 of a basilar membrane (lamina basilaris or membrana basilaris) is stored in a memory of the controller 8. With reference to the model 36, in step 34, a respective arousal or excitation pattern 38 (FIG. 3, FIG. 4) of the basilar membrane is identified for the respective test signal 18 or the narrowband signals thereof 28. The calculation or identification of the excitation pattern 38 takes into account physiological factors, particularly auditory masking, as well as, for example, hearing loss or hearing damage of the affected person 6. The excitation pattern 38 and the respective test signal 18 are then stored in a memory 40.

In a step 42, a probability correlation 44 is established for determining the tinnitus noise 4 based on the test signals 18 and excitation patterns 38 stored in the memory 40. In other words, in particular, similarities among the test signals 18 of the positive comparison results 20b are determined by means of the probability correlation 44, and in this way an evaluation is made of the test signal 18 that best masks, and thus best represents, the tinnitus noise 4.

The comparison 32 and the steps 34 and 42 as well as the storage in the memory 40 of the test signal 18 and the excitation pattern 38 form, in substance, a shared step 46. These steps 46 and 26 are carried out repeatedly until the probability correlation 44 reaches or exceeds a stored threshold value 50 in a threshold value comparison 48. In other words, after steps 26 and 46, the threshold value comparison 48 is performed and the probability correlation 44 is compared with the stored threshold value 50.

The threshold value 50 substantially corresponds to a minimum number of positive comparison results 20b or a minimum number of stored test signals 18 and/or excitation patterns 38, which are needed in order to identify a suitable probability correlation 44. In this case, a "suitable probability correlation 44" refers in particular to a probability correlation 44 having a certain minimum probability that a test signal 18 derived from that probability correlation will mask the tinnitus noise 4. This means that, at the outset of the method, the amplitudes 30 of the narrowband signals 28 of the test signal 18 are set randomly after each comparison 32, and in particular an excitation pattern 38 is calculated for each positive comparison result 20b and correlated with the excitation patterns 38 of preceding comparison results 20a, 20b.

In the case of a negative comparison result 52a from the threshold value comparison 48, in which the probability correlation 44 does not reach or exceed the threshold value 50, a new test signal 18 with random amplitudes 30 of the narrowband signals 28 is generated in step 26 and played back to the affected person 6 in the comparison 32, and the steps 26 and 46 are thus repeated.

In the case of a positive comparison result 52b of the threshold value comparison 48, in which the probability correlation 44 reaches or exceeds the threshold value 50, a second threshold value comparison 54 of the probability correlation 44 is performed using a second stored threshold value 56. The second threshold value 56 is a probability value that indicates how probable a test signal 18 derived from the probability correlation 44 reproduces the actual tinnitus noise 4. In other words, the second threshold value 56 is a measure of the extent to which the test signal 18 derived from the probability correlation 44 corresponds to the tinnitus noise 4. The threshold value 56 is dimensioned, for example, to a probability of 90%. If the probability correlation 44 reaches or exceeds the threshold value 56 in the case of a positive comparison result 58a, the method terminates at a final step 60.

In the case of a negative comparison result 58b, in which the probability correlation 44 does not reach the threshold value 56, a step 62 is started. In step 62, the amplitudes 30 of the narrowband signals 28 are adjusted with reference to the probability correlation 44. The test signal 18 generated in this way is subsequently presented to the affected person 6 in the comparison 32.

Thus, in substance, the method is split into two parts. In an initial phase, the steps 26 and 46 are carried out repeatedly, and each time, the affected person 6 is presented with a test signal 18 in which the amplitudes 30 of the narrowband signals 28 are randomly set. If the comparison results 20b are sufficiently positive, i.e. if a sufficient quantity of test signals 18 and excitation patterns 38 are stored in the memory 40, the probability correlation 44 established on that basis will reach or exceed the threshold value 50 in the threshold value comparison 48.

After this initial phase, starting with the comparison result 52b, an end phase of the method begins, in which the test signal 18 is influenced and adjusted selectively by means of the probability correlation 44. In the end phase, instead of steps 26 and 46, steps 62 and 46 are repeatedly carried out, and thus the comparison results 20b or test signals 18 and excitation patterns 38 are supplied to the memory 40 in increasing numbers. By this means, the probability correlation 40 is successively improved until the threshold value 56 is reached or exceeded in the threshold value comparison 54. In the final step 60, the test signal 18 derived from the probability correlation 40 is output and/or stored, its narrowband signals 28 and amplitudes 30 corresponding in substance to the amplitudes 16 and tinnitus frequencies 14 of the tinnitus noise 4.

Figure 3:
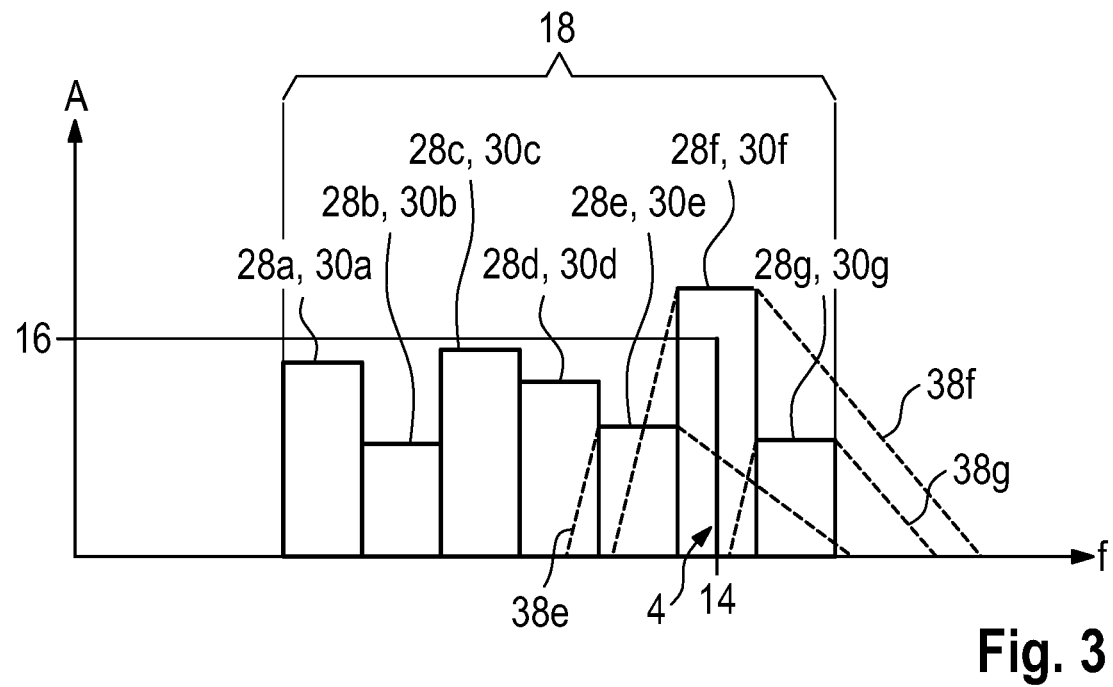
FIG. 3 is a frequency-amplitude diagram of a first test signal and a tinnitus noise as well as a first excitation pattern.
Figure 4:
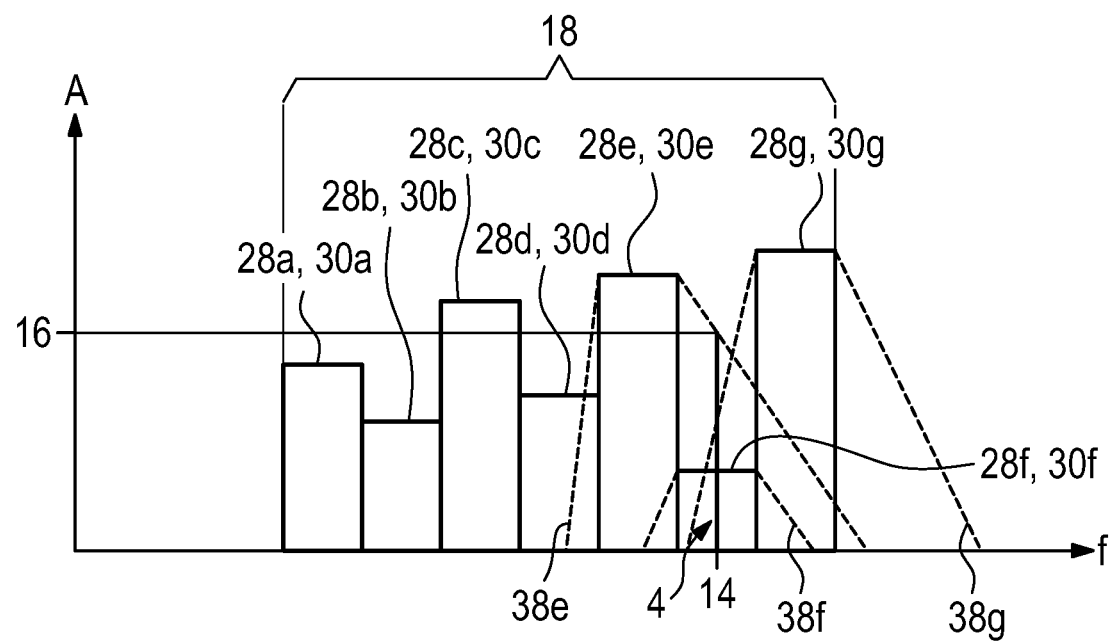
FIG. 4 is a frequency-amplitude diagram of a second test signal and the tinnitus noise as well as a second excitation pattern.

FIGS. 3 and 4 respectively show a frequency-amplitude diagram.

The frequency f is plotted along the horizontal x-axis (abscissa) of the diagram, and the amplitude A is plotted along the vertical y-axis (ordinate) of the diagram.

FIG. 3 and FIG. 4 each respectively show a test signal 18 with seven narrowband signals 28, which are assigned reference numerals a to g below, and also show the tinnitus noise 4, which in this example consists only of a tinnitus frequency 14 with amplitude 16. The narrowband signals 28a to 28g each respectively have the associated amplitude 30a to 30g. For the narrowband signals 28e and 28f as well as 28g, a respective excitation pattern 38e, 38f, 38g is additionally shown in dotted lines.

In the exemplary embodiments of FIGS. 3 and 4, the tinnitus noise 4 is arranged in the frequency range of the narrowband signal 28f of the test signals 18.

The test signal 18 of the exemplary embodiment of FIG. 3 masks the tinnitus noise 4 because the narrowband signal 28f has a greater amplitude 30f than the tinnitus noise 4. In the comparison 32, a positive comparison result 20b is effected in this way, and as a result the test signal 18 as well as the corresponding excitation pattern 38 are stored in the memory 40.

The test signal 18 of the exemplary embodiment of FIG. 4 also masks the tinnitus noise 4. Although the narrowband signal 28f has too low an amplitude 30f to mask the tinnitus noise 4 by itself, the nearby narrowband signals 28e and 28g cause auditory masking so that the affected person 6 does not perceive the tinnitus noise 4. This auditory masking is described by the overlapping excitation patterns 38e, 38f and 38g. In this exemplary embodiment, the auditory masking is effected in particular by the narrowband signal 28e or the excitation pattern 38e. Thus, in the comparison 32, a positive comparison result 20b is also effected for the test signal 18 of FIG. 4; consequently, the test signal 18 and corresponding excitation patterns 38 are stored in the memory 40.

By additionally identifying and considering the excitation pattern 38 in the course of establishing the probability correlation 44, it is made possible to use broadband test signals 18 and to reliably identify both the individual tinnitus frequencies 14 and the amplitudes thereof 16 in the tinnitus noise 4.

The invention is not limited to the above-described exemplary embodiment. Rather, other variants of the invention may be derived therefrom by a person of ordinary skill in the art without departing from the subject matter of the invention. In particular, all the individual features described in connection with the exemplary embodiment may also be combined with each other in other ways without departing from the subject matter of the invention.

In an alternative embodiment, or example, tone complexes or tone components are used instead of narrowband signals 28. The number of tone components used, in this case, depends substantially on the intensity of the tinnitus that needs to be recognized, and may also depend on a hearing loss-dependent width of the excitation pattern on the basilar membrane. For example, if the intensity of tinnitus is comparatively slight and the width of the excitation of the basilar membrane is comparatively great, the method may be carried out with a reduced number of tone components in the test signal 18.

Tinnitus that is perceived as a tone often occurs at frequencies between 1 kHz and 11 kHz, in particular between 500 Hz and 11 kHz. In an advantageous development, the bandwidth of the test signal 18 may additionally or alternatively be reduced, based on the probabilities of such a tinnitus perception.

The following is a summary list of reference numerals and the corresponding structure used in the above description of the invention:

2 Apparatus
4 Tinnitus noise
6 Affected person
8 Controller
10 Display unit
12 Headphone
14 Tinnitus frequency
16 Tinnitus amplitude/amplitude
18 Test signal
20a, 20b Comparison result
22 Image data
24 Start
26 Step
28, 28a, 28b, 28c, 28d, 28e, 28f, 28g Signal frequency/narrowband signal
30, 30a, 30b, 30c, 30d, 30e, 30f, 30g Signal amplitude/amplitude
32 Comparison
34 Step
36 Model
38, 38e, 38f, 38g Excitation pattern
40 Memory
42 Step
44 Probability correlation
46 Step
48 Threshold value comparison
50 Threshold value
52a, 52b Comparison result
54 Threshold value comparison
56 Threshold value
58a, 58b Comparison result
60 Final step
62 Step
f Frequency
A Amplitude

The invention claimed is:

1. A method for operating an apparatus for tinnitus characterization, which comprises the steps of:
performing a first step which comprises the substeps of:
generating, via a signal generator, a broadband test signal having a plurality of narrowband signal frequencies disposed adjacent to each other;
outputting the broadband test signal to a user for masking a tinnitus noise;
comparing the broadband test signal with the tinnitus noise to determine a masking effect the broadband test signal has on the tinnitus noise;
storing the broadband test signal with an associated comparison result in a memory of a controller; and
determining a probability correlation for determining the tinnitus noise based on stored broadband test signals and associated comparison results, wherein in a case of a positive comparison result where the tinnitus noise is masked by the broadband test signal, the probability correlation for determining the tinnitus noise based on a correlation among commonalities of all positive comparison results being determined from the stored broadband test signals and the associated comparison results;
performing a second step which varies amplitudes of individual ones of the signal frequencies of the broadband test signal via a random number generator of the controller;
repeatedly performing the first and second steps until the probability correlation reaches or exceeds a first threshold value, wherein the first threshold value corresponding to a minimum number of the positive comparison results having a minimum probability that the broadband test signal derived from the probability correlation masks the tinnitus noise;
performing a third step which varies the amplitudes of individual ones of the signal frequencies of the broadband test signal with reference to the probability correlation resulting in a modified broadband test signal; and
repeating the first and third steps with the modified broadband test signal having the signal frequencies with varied amplitudes based on the probability correlation until the probability correlation reaches or exceeds a second threshold value and storing the modified broadband test signal-in the memory.

2. The method according to claim 1, which further comprises during the second step, setting randomly the amplitudes of individual ones of the signal frequencies of the broadband test signal.

3. The method according to claim 1, which further comprises using a physiological model to determine the probability correlation.

4. The method according to claim 3, which further comprises using a model of a basilar membrane as the physiological model, the probability correlation being determined on a basis of an excitation pattern of the model of the basilar membrane.

5. An apparatus for tinnitus characterization, comprising:
a signal generator;
a controller having a memory and a random number generator, said controller programmed to:
perform a first step which comprises the substeps of:
  generate, via said signal generator, a broadband test signal having a plurality of narrowband signal frequencies disposed adjacent to each other;
  output the broadband test signal to a user for masking a tinnitus noise;
  compare the broadband test signal with the tinnitus noise to determine a masking effect the broadband test signal has on the tinnitus noise;
  store the broadband test signal with an associated comparison result in said memory of said controller; and
  determine a probability correlation for determining the tinnitus noise based on stored broadband test signals and associated comparison results, wherein in a case of a positive comparison result where the tinnitus noise is masked by the broadband test signal, the probability correlation for determining the tinnitus noise based on a correlation among commonalities of all positive comparison results being determined from the stored broadband test signals and the associated comparison results;
perform a second step which varies amplitudes of individual ones of the signal frequencies of the broadband test signal via said random number generator, wherein the first threshold value corresponding to a minimum number of the positive comparison results having a minimum probability that the broadband test signal derived from the probability correlation masks the tinnitus noise;
repeatedly perform the first and second steps until the probability correlation reaches or exceeds a first threshold value;
perform a third step which varies the amplitudes of individual ones of the signal frequencies of the broadband test signal with reference to the probability correlation resulting in a modified broadband test signal; and
repeating the first and third steps with the modified broadband test signal having the signal frequencies with varied amplitudes based on the probability correlation until the probability correlation reaches or exceeds a second threshold value and storing the modified broadband test signal in the memory.

* * * * *